United States Patent
Phillips et al.

(10) Patent No.: US 8,301,227 B2
(45) Date of Patent: Oct. 30, 2012

(54) TISSUE MARKING SYSTEM AND METHOD

(75) Inventors: Michael Phillips, Oconomowoc, WI (US); Janet Phillips, Oconomowoc, WI (US)

(73) Assignee: Vector Surgical, LLC, Waukesha, WI (US)

( * ) Notice: Subject to any disclaimer, the term of this patent is extended or adjusted under 35 U.S.C. 154(b) by 1464 days.

(21) Appl. No.: 11/749,552

(22) Filed: May 16, 2007

(65) Prior Publication Data

US 2007/0270681 A1    Nov. 22, 2007

Related U.S. Application Data

(60) Provisional application No. 60/800,714, filed on May 16, 2006.

(51) Int. Cl.
*A61B 17/00* (2006.01)
(52) U.S. Cl. ........................ 600/426; 606/151
(58) Field of Classification Search .................. 600/426; 606/151
See application file for complete search history.

(56) References Cited

U.S. PATENT DOCUMENTS

| | | | |
|---|---|---|---|
| 5,474,569 A | 12/1995 | Zinreich et al. | |
| 5,667,526 A * | 9/1997 | Levin | 606/207 |
| 5,902,310 A * | 5/1999 | Foerster et al. | 606/142 |
| 6,247,211 B1 | 6/2001 | Bell | |
| 6,826,257 B2 | 11/2004 | Sayre et al. | |
| 7,657,300 B2 * | 2/2010 | Hunter et al. | 600/424 |
| 2003/0204137 A1 * | 10/2003 | Chesbrough et al. | 600/426 |
| 2006/0229529 A1 | 10/2006 | Wright | |

* cited by examiner

*Primary Examiner* — Parikha Mehta
(74) *Attorney, Agent, or Firm* — Barbara A. Wrigley; Oppenheimer Wolff & Donnelly LLP (57) ABSTRACT

A tissue marking system is configured to mark a tissue sample. The tissue marking system includes an actuator portion movable between an actuated position and a non-actuated position and a jaw portion coupled to the actuator portion and movable between an open position and a closed position in response to movement of the actuator portion from the actuated position to the non-actuated position. The jaw portion includes a first tooth and a second tooth configured to engage the tissue sample when the jaw portion moves from the open position to the closed position.

26 Claims, 5 Drawing Sheets

TISSUE MARKING SYSTEM AND METHOD

RELATED APPLICATION DATA

This application claims benefit under 35 U.S.C. Section 119(e) of U.S. Provisional Application No. 60/800,714, filed May 16, 2006, which is fully incorporated herein by reference.

BACKGROUND

The present invention relates to a tissue marking system that is visible during radiographic examination. More particularly, the present invention relates to a tissue marking system that identifies tissue orientation during both radiographic and visual examination.

During surgery, it is often necessary to remove a sample of tissue and closely examine that tissue sample (e.g., radiographic examination) while knowing its original orientation within the patient. For example, cancerous tumors are often removed from the patient and then examined to verify that a sufficient margin of tissue surrounding the tumor has been removed. To determine this, the tissue sample is examined and the margins on each surface are identified. Should a margin be insufficient, it is important for the surgeon to know the orientation of the sample to allow for the removal of additional tissue in the proper area.

Presently, different color sutures, different length sutures, or different quantities of sutures are inserted into the tissue sample to identify the orientation of the tissue. However, this is time consuming and the sutures can be accidentally removed making identification of the tissue orientation difficult. Furthermore, sutures are not visible in radiographic (X-ray) images. As such, the tissue sample must be marked in a second way to provide for orientation in any X-ray images that may be taken.

SUMMARY

In one construction, the invention provides a tissue marking system configured to mark a tissue sample. The tissue marking system includes an actuator portion movable between an actuated position and a non-actuated position and a jaw portion coupled to the actuator portion and movable between an open position and a closed position in response to movement of the actuator portion from the actuated position to the non-actuated position. The jaw portion includes a first tooth and a second tooth configured to engage the tissue sample when the jaw portion moves from the open position to the closed position.

In another construction, the invention provides a tissue marking system configured to mark a tissue sample. The tissue marking system includes a first clip having a first jaw portion movable between a closed position and an open position. The first jaw portion is configured to engage the tissue sample when moved from the open position to the closed position. A first radiographic indicator is coupled to the first clip and includes first indicia that is opaque to radiographic examination. A second clip includes a second jaw portion movable between a closed position and an open position. The second jaw portion is configured to engage the tissue sample when moved from the open position to the closed position. A second radiographic indicator is coupled to the second clip and includes second indicia that is opaque to radiographic examination. The second indicia is different from the first indicia.

In yet another construction, the invention provides a method of marking the orientation of a tissue sample. The method includes actuating a first clip to move a first jaw portion from a closed position to an open position and positioning the first clip adjacent a first surface to be marked, the first clip including first indicia. The method also includes releasing the first clip to allow the first jaw to move from the open position to the closed position to engage the tissue sample, actuating a second clip to move a second jaw portion from a closed position to an open position, and positioning the second clip adjacent a second surface to be marked, the second clip including second indicia different from the first indica. The method further includes releasing the second clip to allow the second jaw to move from the open position to the closed position to engage the tissue sample.

Thus, the invention provides a system for use in marking the orientation of a tissue sample. The invention includes clips that are attachable to a tissue sample and that are at least partially opaque in the X-ray region of the electromagnetic spectrum. The clips include teeth that engage the tissue sample and remain engaged during the X-ray process.

The invention also provides a method of marking the orientation of a tissue sample for radiographic examination. The method includes attaching clips that are at least partially opaque in the X-ray region of the electromagnetic spectrum to the tissue sample at three different points. In some constructions, the surfaces of the tissue sample to which the clips are attached are also marked, such as with ink, for visual examination.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

Figure 1:
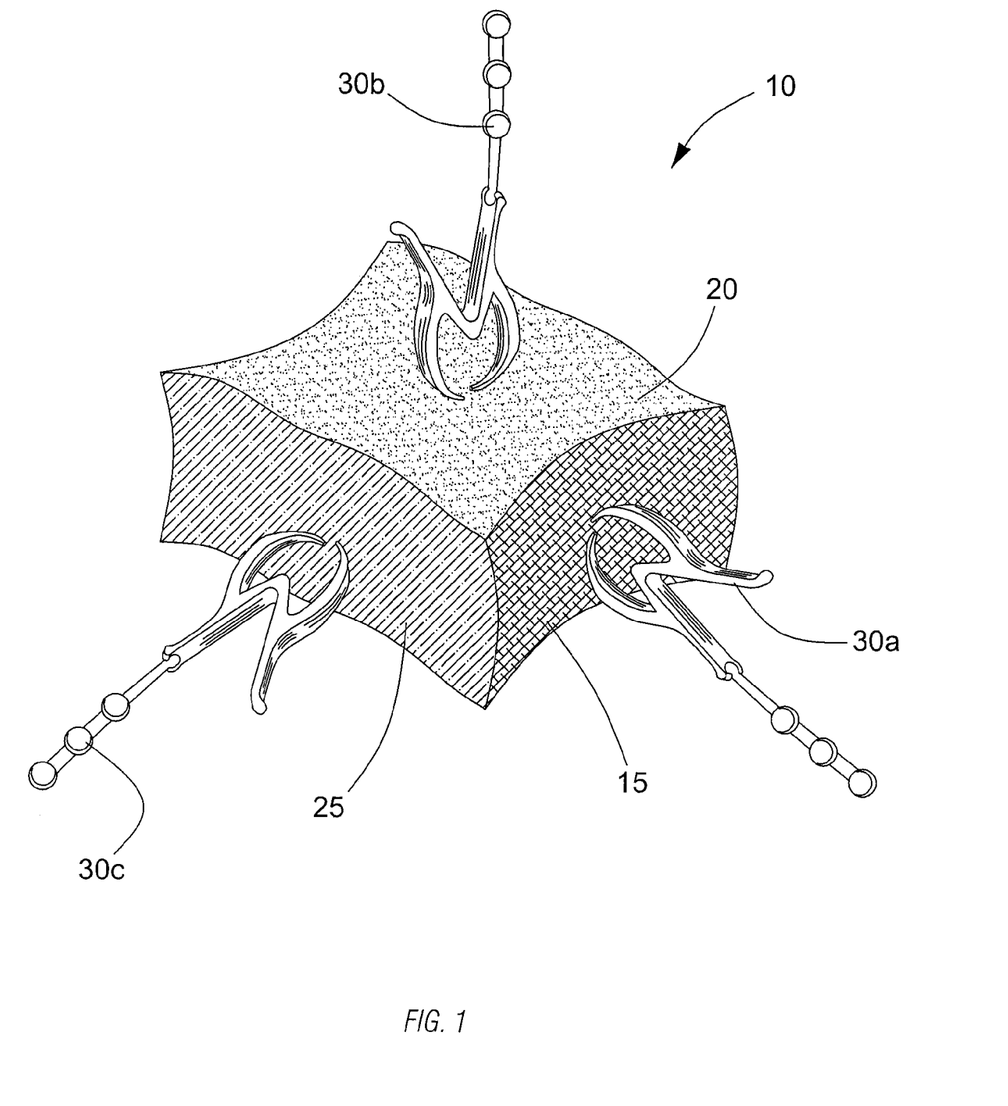
FIG. 1 is a perspective view of a tissue sample after being removed from a patient.

With reference to FIG. 1, an example of a potential tissue sample 10 is illustrated. A substantially cubical sample 10 is illustrated for the sake of discussion. However, one of ordinary skill in the art will realize that the shape of a tissue sample is generally not cubical but rather is irregular and may more typically resemble an irregular sphere. The invention described herein is applicable to many tissue samples 10 in which orientation is important. For example, breast cancer requires that a tissue sample 10 be removed, and that its orientation be identified to verify that sufficient margin has been removed. As such, the invention should not be limited only to the uses described herein as it is well suited for use with any tissue that requires orientation for pathology and/or radiology. These tissues include but are not limited to samples of breast, bone, thyroid, lymph nodes, brain, sarcomas, kidney, bowel, spleen, soft tissue masses, melanoma, squamous cell skin cancer, basal cell cancer, liver tumors, and the like.

As discussed, many different systems are available for marking the tissue sample 10 for visual examination (e.g., different color sutures, different length sutures, different quantity of sutures, etc.). In a preferred construction, the tissue sample 10 is marked using an ink system. The ink system has several advantages over the other systems discussed herein. For example, an ink system allows for an entire plane to be identified rather than just a point. In addition, the ink systems are generally much faster than the prior methods discussed. Furthermore, the ink systems do not present the risk of punctures that may be present with the suture systems. One suitable ink system is described in U.S. patent application Ser. No. 10/978,948, filed Nov. 1, 2004, and fully incorporated herein by reference.

FIG. 1 illustrates the tissue sample 10 after removal from a patient and after being marked with three different color inks 15, 20, 25. Each color ink 15, 20, 25 is represented by a different cross hatch pattern. While any three planes or surfaces of the tissue sample 10 can be used to identify the orientation of the sample 10, it is preferred that three substantially orthogonal surfaces, or an area of concern be identified.

Before proceeding, it should be noted that the term "ink" as used herein is meant to encompass any coloring element that can be applied to a tissue sample 15, with dye, paint, and stains being a few examples. As such, the invention should not be limited to ink alone.

Once the tissue sample 10 is marked as just described, a visual inspection can be made with the orientation being easily identifiable. However, none of the marking systems discussed herein will appear in an X-ray. As such, a different marking system is required to allow for the use of radiological examinations that can identify orientation in the captured images.

Figure 2:
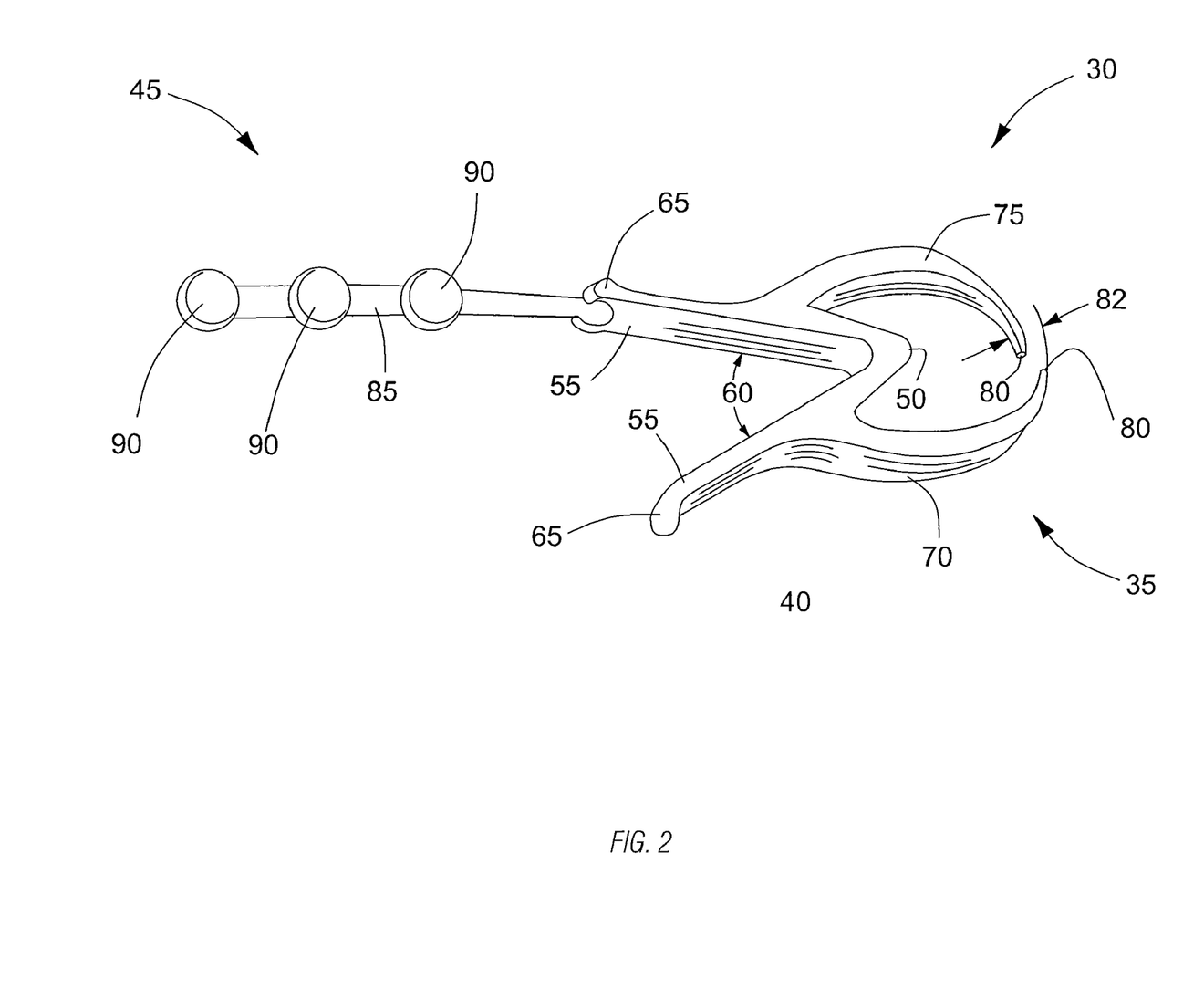
FIG. 2 is a front perspective view of a clip that is attachable to the tissue sample of FIG. 1.
Figure 3:
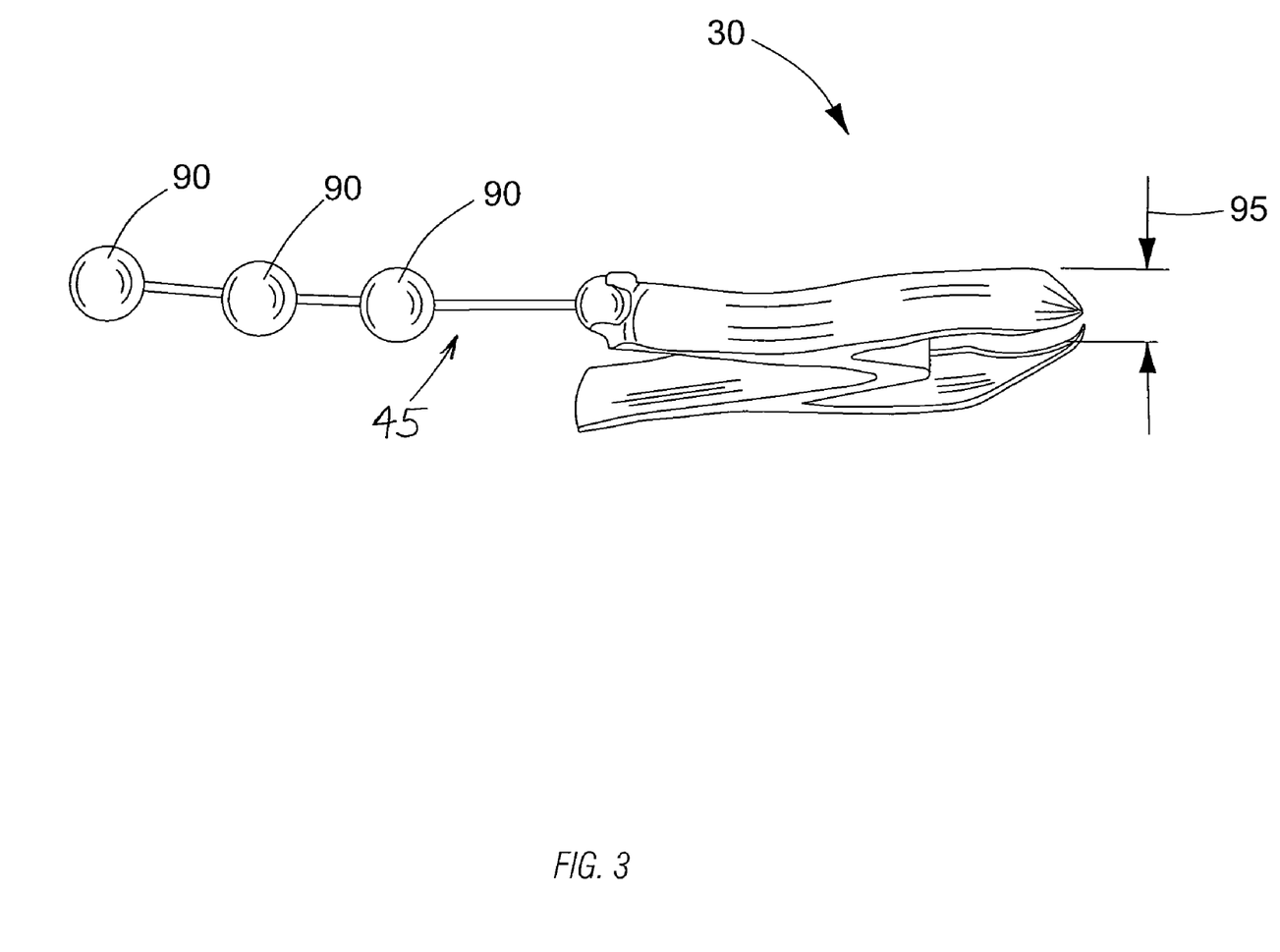
FIG. 3 is top perspective view of the clip of FIG. 2.

FIGS. 2 and 3 illustrate one construction of a clip 30 that directly engages a tissue sample 10 to identify the orientation of the tissue sample 10 in an X-ray. In preferred constructions, most or all the clip 30 is transparent or translucent in the X-ray region of the electromagnetic spectrum. This allows an X-ray to be taken through the clips 30 such that they do not interfere with the image. The clip 30 includes a jaw portion 35, an actuator portion 40, and a tail 45. The actuator portion 40 is substantially V-shaped and includes an apex 50 and two arms 55 that connect with one another at the apex 50. In the illustrated construction, the two arms 55 cooperate to define an angle 60 of about 45 degrees with other angles 60 also being possible.

In some constructions, the arms 55 include a knob 65 positioned at the end of the arm 55 opposite the apex 50. The knobs 65 make it easier to grasp and actuate the actuator portion 40 without the clip 30 slipping from the user's hand or an instrument. In still other constructions, a texture such as ridges or other grip-enhancing surfaces may be formed on the arms 55 to reduce the likelihood of slippage during actuation.

The jaw portion 35 includes two teeth 70, 75 with each tooth 70, 75 extending from one of the arms 55 of the actuator portion 40. Each tooth 70, 75 is substantially curved and terminates at a point 80. The curve of each of the teeth 70, 75 is such that the two points 80 are pointing substantially toward one another when the clip 30 is in the non-actuated position.

One of the teeth 70 is slightly longer than the other tooth 75 such that the teeth 70, 75 cooperate to produce a slight overbite 82. The overbite 82 improves the grip of the teeth 70, 75 in the tissue sample 10, thereby making it less likely that the clip 30 would be accidentally removed from the sample 10.

In some constructions, barbs or other tissue-engaging members could be formed as part of the teeth 70, 75 to further enhance their grip on the tissue sample 10 to which they are attached. In addition, more than two teeth 70, 75 or teeth 70, 75 having more than one point 80 could also be employed if desired.

Each tooth 70, 75 defines a tooth surface area at the tooth tip. The surface area is related to the biasing force produced by the clip 30. Specifically, the tooth tip surface area is sized to not puncture a glove when only the biasing force of the clip is applied. Thus, when clips with larger biasing forces are employed, larger tooth tip surface areas are employed.

Each tooth 70, 75 attaches to one of the arms 55 of the actuator portion 40 approximately one-third of the length back from the apex 50. The attachment point of the teeth 70, 75 to the arms 55 determines how far open, or apart the points 80 will spread when the clip 30 is in the actuated position. Thus, other constructions could position the teeth 70, 75 further away from the apex 50 and/or could increase the angle 60 defined by the arms 55 to increase the opening between the points 80. Likewise, the opposite arrangement could be employed to reduce the opening if desired.

The tail 45 extends from one of the arms 55 of the actuator portion 40 and includes an indicator 85 that is opaque in an X-ray region of the electromagnetic spectrum. In the illustrated construction, the indicator 85 includes a number of balls 90 formed as part of the tail 45. The balls 90 are substantially opaque in the X-ray region of the electromagnetic spectrum. As such, the balls 90 appear white on an X-ray. In this construction, the number of balls 90 on the tail 45 indicates orientation. For example, as illustrated in FIG. 1, one surface of the sample 10 may have a clip 30a attached with one ball 90 on the tail 45. The second surface would then include a clip 30b with two balls 90, and the third surface would include a clip 30c with three balls 90. Because the clips 30a, 30b, 30c and the tails 45 travel with the sample 10, multiple X-rays at multiple angles can be taken without losing the ability to determine the orientation of the tissue sample 10.

While clips 30 with tails 45 having one, two, or three balls 90 can be provided, one construction employs tails 45 with only three balls 90. The user then breaks off one ball 90 or two balls 90 to define the different indicators 85. Furthermore, while the tail 45 is shown and described as being attached to one of the arms 55, it could be attached to nearly any portion of the actuator portion 40 or the jaw portion 35 if desired.

In other constructions, other indicators 85 may be employed. For example, one construction uses different shaped indicators (e.g., square, rectangular, triangular, etc.) for each clip used to identify orientation (i.e., three clips). Still other constructions may employ indicators that vary by size. For example, one construction could employ a single large ball, a single medium size ball, and a single small ball (or no ball) to indicate orientation.

Figure 4:
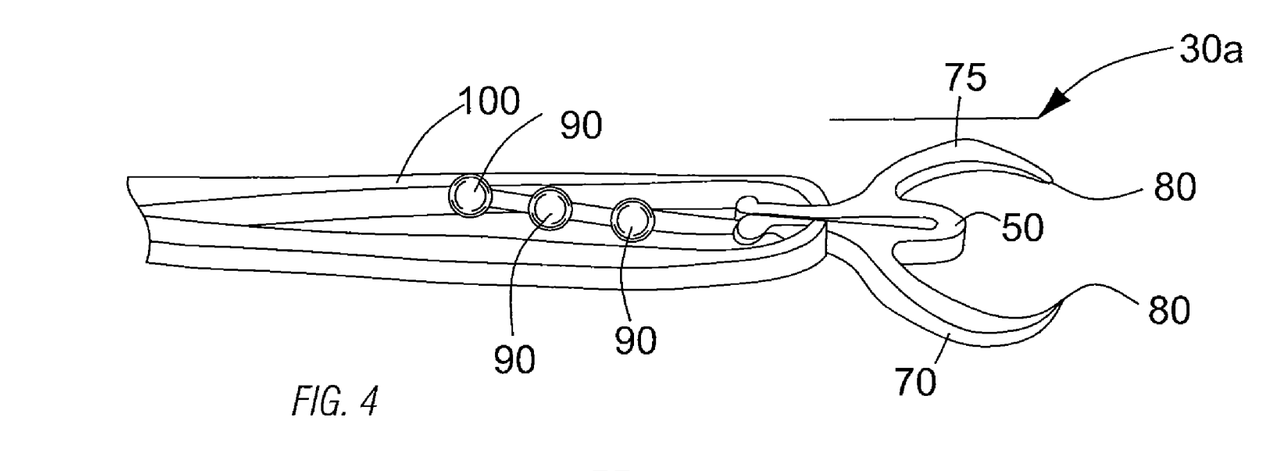
FIG. 4 is a front perspective view of the clip of FIG. 2 in an actuated position.
Figure 5:
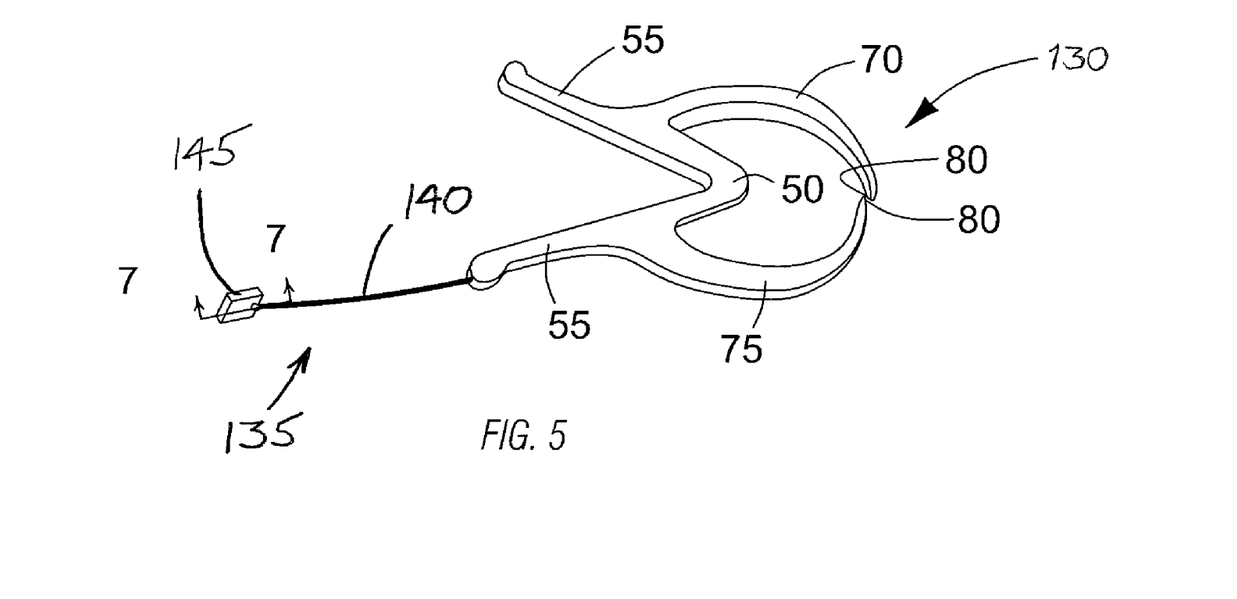
FIG. 5 is a front perspective view of another clip in a non-actuated position.

FIG. 5 illustrates yet another construction of a clip 130 that is suitable for use in identifying the orientation of a tissue sample. The clip 130 is similar to the clips 30a, 30b, 30c of FIGS. 1-4 with the exception of a tail 135. The tail 135 includes an extension portion 140 that connects to one of the arms 55 or some other portion of the clip 130, and an identifier portion 145 that is attached to the extension portion 140.

Figure 6:
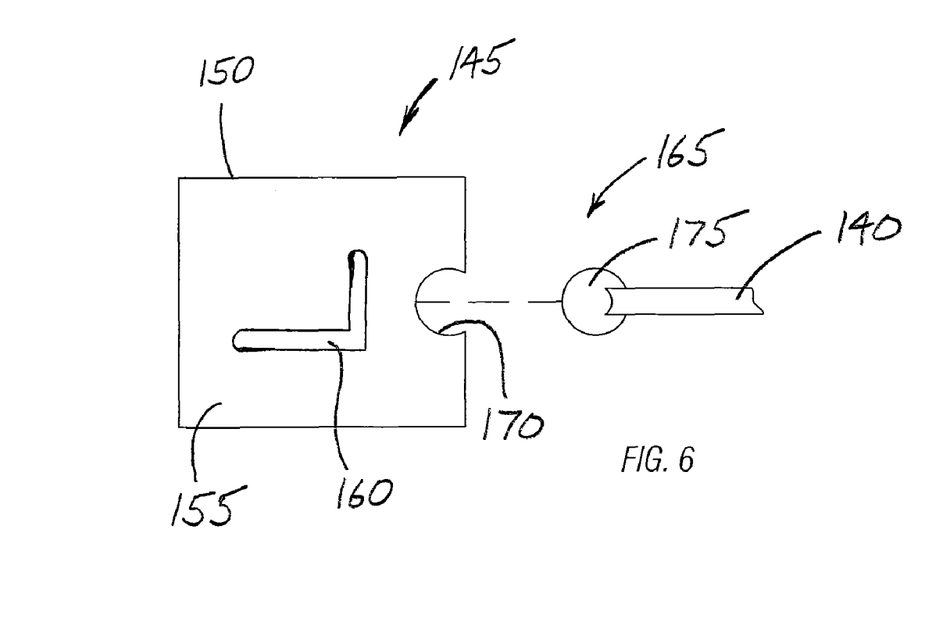
FIG. 6 is an exploded front view of a portion of the clip of FIG. 5.

In the illustrated construction, the extension portion 140 is fixedly attached to the arm 55. In preferred constructions, the extension portion 140 is integrally-formed as part of the arm 55 or clip 130. As illustrated in FIG. 6, the identifier portion 145 includes a substantially plate-shaped member 150. The plate-shaped member 150 defines two relatively large planar surfaces 155 that facilitate the placement of indicia 160 that aids in identifying the orientation of the sample 10 to which the clip 130 is attached. For example, an "L" is placed on one of the planar surfaces 155 to indicate a lateral position. The "L" (Lateral) can be placed on the planar surface 155 using a metallic paint or other system that is visible in an X-ray image. Some other indicia that may be employed includes A for Anterior/Superficial, P for Posterior/Deep, S for Superior/Cephalad, I for Inferior/Caudal, and/or M for Medial. Of course other indicia could be employed so long as the surgeon and the radiologist or pathologist understand their meaning.

Figure 7:
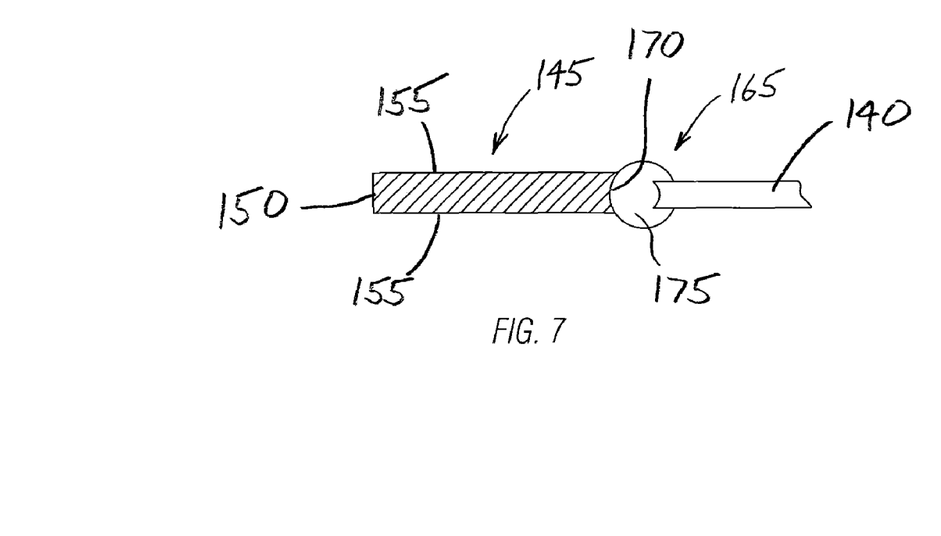
FIG. 7 is a section view of a portion of the clip of FIG. 5 taken along line 7-7 of FIG. 5.

As illustrated in FIGS. 6 and 7, the identifier portion 145 attaches to the extension portion 140 using a ball-and-socket joint 165. In the illustrated construction, a socket 170 is formed in the identifier portion 145 and a ball 175 is formed at the end of the extension portion 140. The ball 175 fits within the socket 170 and allows movement of the identifier portion 145 with respect to the extension portion 140 and the remainder of the clip 130.

Thus, the clip 130 of FIGS. 5-7 includes an identifier portion 145 that is articulatable with respect to the remainder of the clip 130 to which it is attached. In one construction, the identifier portion 145 is articulatable with respect to the extension portion 140. In another construction, the extension portion 140 is articulatable with respect to the remainder of the clip 130 and the identifier portion 145 is fixed with respect to the extension portion 140. In this construction, the ball-and-socket joint 165, or other joint is formed between the arm 55 and the extension portion 140 similar to the one illustrated in FIG. 2. In still other constructions, both the extension portion 140 and the identifier portion 145 are articulatable with respect to the remainder of the clip 130. These constructions would employ two joints. As one of ordinary skill in the art will recognize, each of these examples describe an arrangement in which the identifier portion 145 is articulatable with respect to the remainder of the clip 130 to allow an X-ray technician to position the identifier portion 145 for optimum viewing in an X-ray image.

One of ordinary skill in the art will realize that many different indicators 85 can be employed so long as they are easily identifiable from any angle on an X-ray image. In addition, while only three clips 30, 130 are required to define an orientation, any number of clips 30, 130 can be employed (e.g., six clips. In addition, a single clip can be employed if desired to identify an area of interest rather than a tissue orientation.

As illustrated in FIG. 3, a width 95 of the clip 30 is small enough to allow the tissue sample 10 and the clip 30 to be compressed during the X-ray process without affecting the connection of the clip 30 and without the clips 30 interfering with the process.

In preferred constructions, the actuator portion 40 and the jaw portion 35 are integrally-formed as a single component. For example, in one construction, the actuator portion 40 and the jaw portion 35 are injection molded as a single part in one manufacturing step. By integrally-molding the actuator portion 40 and the jaw portion 35, the overall cost of the clip 30 is reduced.

In more preferred constructions, the actuator portion 40, the jaw portion 35, and the tail 45 or a portion of the tail 45 are integrally-formed as a single component. In these constructions the actuator portion 40, the jaw portion 35, and the tail 45 can be made from one material in a single injection molding step. Alternatively, two different materials could be used with the actuator portion 40 and the jaw portion 35 being made from a material that is translucent in the X-ray region of the electromagnetic spectrum, and the tail 45 being made from a more opaque material. In these constructions, a co-molding or two step injection molding process may be employed.

With reference to FIGS. 1, 4, and 5, the use of the clip 30 will be described. Once the tissue sample 10 is removed from the patient, the surfaces to be marked are identified. The actuator portion 40 of the first clip 30a is grasped and compressed to move the clip 30a into the actuated position as shown in FIG. 4. It should be noted that FIG. 4 illustrates an Alice Clamp 100 holding the clip 30a in the actuated position. However, the clip 30a can also be actuated using other surgical instruments (e.g., clamps, forceps, etc.) or a user's fingers. Once in the actuated position, the points 80 of the teeth 70, 75 are positioned adjacent the surface of the tissue sample 10 to be marked and the actuator portion 40 is released. Once released, the teeth 70, 75 move to their non-actuated positions and the points 80 engage the tissue sample 10. These steps are repeated for each additional clip 30b, 30c that is attached to the tissue sample 10. Generally, three clips 30a, 30b, 30c are required to identify the orientation of the sample 10. However more or fewer clips 30 can be employed if desired.

When using the clips 130 of FIGS. 5-7, once the clips 130 are attached, an X-ray technician or other user is able to articulate the identifier portions 145 of the various clips 130 to provide optimum viewing in any X-ray images. Thus, the X-ray technician is able to reorient the tissue sample 10 as desired without worrying about losing the orientation and with the knowledge that the identifier portions 145 can be reoriented as required to provide the optimum view of the indicia 160 in any X-ray images.

While the clips 30 can be used as just described to mark the orientation of the tissue sample 10, in a more preferred use, the clips 30 are used in conjunction with an ink marking system. In this use, the three surfaces to be marked are first marked with ink 15, 20, 25. Clips 30a, 30b, 30c are then placed in the same three surfaces, or different surfaces if desired, to further mark the orientation of the tissue sample 10.

In one construction, the clips 30a, 30b, 30c are provided with the ink system and are color coded to match the ink colors 15, 20, 25. Thus, the tissue sample 10 is marked with ink 15, 20, 25 and the clips 30a, 30b, 30c are then attached to the surface of the tissue sample 10 corresponding to their particular color.

Once the tissue sample 10 is marked with both ink and the clips 30, both X-ray and visual inspection can be performed without confusing the orientation of the tissue sample 10.

Thus, the invention provides, among other things, a new and useful marking system for use in marking the orientation of a tissue sample 10. The constructions of the clip 30 and the methods of using the clip 30 described above and illustrated in the figures are presented by way of example only and are not intended as a limitation upon the concepts and principles of the invention.

What is claimed is:

1. A tissue marking system configured to mark a tissue sample, the tissue marking system comprising:

an actuator portion, said actuator portion movable between an actuated position and a non-actuated position;

a jaw portion coupled to the actuator portion and movable between an open position and a closed position in response to movement of the actuator portion from the non-actuated position to the actuated position, the jaw portion including a first tooth and a second tooth configured to engage the tissue sample when the jaw portion moves from the open position to the closed position;

a coupling mechanism on one of said actuator portion and said jaw portion; and a radiographic indicator configured to be received by said coupling mechanism, and further configured to rotate within said coupling mechanism relative to said one of said actuator portion and said jaw portion during an imaging procedure.

2. The tissue marking system of claim 1, wherein the first tooth includes a first tip and the second tooth includes a second tip, and wherein the first tip is offset a non-zero distance from the second tip to define an overbite when the jaw portion is in the closed position.

3. The tissue marking system of claim 1, wherein the actuator portion includes a first arm and a second arm connected to the first arm to define an apex.

4. The tissue marking system of claim 3, wherein the first tooth attaches to the first arm and the second tooth attaches to the second arm.

5. The tissue marking system of claim 1, wherein the radiographic indicator is configured to be identifiable in a radiographic examination.

6. The tissue marking system of claim 5, wherein the radiographic indicator includes an identifier portion coupled to the tail portion, the tail portion rotatably coupled to said coupling mechanism.

7. The tissue marking system of claim 5, wherein the jaw portion and the actuator portion are transparent to radiographic examination, and wherein the indicator portion includes indicia that is opaque to radiographic examination.

8. The tissue marking system of claim 1, wherein the actuator portion comprises a textured surface.

9. The tissue marking system of claim 1, wherein each of the first tooth and the second tooth defines a tooth area, the tooth area sufficiently sized to correspond to a biasing force produced by the actuator portion.

10. A tissue marking system configured to mark a tissue sample, the tissue marking system comprising:
a first clip including a first jaw portion movable between a closed position and an open position, the first jaw portion configured to engage the tissue sample when moved from the open position to the closed position, said first clip including first receiving means thereon;

a first radiographic indicator configured to be received by said first receiving means and including first indicia that is opaque to radiographic examination, and further configured to rotate within said first receiving means during an imaging procedure;

a second clip including a second jaw portion movable between a closed position and an open position, the second jaw portion configured to engage the tissue sample when moved from the open position to the closed position, said second clip including second receiving means thereon; and a second radiographic indicator configured to be received by said second receiving means and including second indicia that is opaque to radiographic examination and that is different from the first indicia, the second indicator being further configured to rotate within said second receiving means during the imaging procedure;

wherein the first clip or the second clip or both clips are transparent to radiographic examination.

11. The tissue marking system of claim 10, wherein the first jaw portion includes a first tooth having a first tip, and a second tooth having a second tip, and wherein the first tip is offset a non-zero distance from the second tip to define an overbite when the first jaw portion is in the closed position.

12. The tissue marking system of claim 11, wherein the first clip includes an actuator portion movable between an actuated position and a non-actuated position, and wherein the actuator portion includes a first arm and a second arm, said first and second arms defining an apex.

13. The tissue marking system of claim 12, wherein the first tooth directly attaches to the first arm and the second tooth directly attaches to the second arm.

14. The tissue marking system of claim 10, further comprising an identifier portion formed with said radiographic indicator.

15. The tissue marking system of claim 10, wherein the first clip includes an actuator portion coupled to the jaw portion, the actuator portion biasing the jaw portion toward the closed position.

16. The tissue marking system of claim 10, further comprising a third clip including a third jaw portion movable between a closed position and an open position, the third jaw portion configured to engage the tissue sample when moved from the open position to the closed position, said third clip including third rotatable receiving means thereon; and a third radiographic indicator rotatably received by said third rotatable receiving means and including third indicia that is opaque to radiographic examination, the third indicia being different from the first indicia and the second indicia.

17. The tissue marking system of claim 10, wherein the first clip comprises a textured surface.

18. The tissue marking system of claim 10, wherein the first clip includes a first tooth and a second tooth that define a tooth area, the tooth area sized in response to a biasing force produced by the first clip.

19. A method of marking an orientation of a tissue sample, the method comprising:
providing a tissue sample to be marked, said tissue sample including three tissue surfaces, each of said tissue surfaces marked with three different colors of ink;

providing at least one clip including a radiopaque marker configured to be coupled thereto, the marker being further configured to rotate within a portion of said at least one clip during an imaging procedure, said clip including a jaw portion;

positioning the at least one clip adjacent one tissue surface to be additionally marked with said at least one clip;

actuating said at least one clip to move the jaw portion to a closed position that engages said tissue surface to be marked; and rotating said radiopaque marker relative to said at least one clip such that the radiopaque marker remains undisturbed upon compression of the tissue sample.

20. The method of claim 19, further comprising radiographically examining the tissue sample, and identifying the orientation of the tissue sample based at least in part on the position of the radiopaque marker.

21. A tissue marking system configured to mark a tissue sample, the tissue marking system comprising a clip, said clip including:
an actuator portion including two arms, at least one of said two arms including a coupling mechanism thereon, said actuator portion movable between an actuated position and a non-actuated position;

an indicator having a tail portion including a ball formed on an end thereof, said ball configured to engage and rotate within said coupling mechanism;

a jaw portion coupled to the actuator portion and movable between an open position and a closed position in response to movement of the actuator portion from the actuated position to the non-actuated position, the jaw portion including a first tooth and a second tooth configured to engaged the tissue sample when the jaw portion moves from the open position to the closed position, wherein said jaw portion and said actuator portion are transparent to radiographic examination.

22. The tissue marking system of claim 21 said first tooth having a first tip and said second tooth having a second tip, wherein the first tip is offset a non-zero distance from the second tip to define an overbite when the jaw portion is in the closed position.

23. The tissue marking system of claim 21 wherein said tail portion further includes an indicator.

24. The tissue marking system of claim 21 wherein said jaw portion and said actuator portion are transparent in an X-ray region of an electromagnetic spectrum.

25. The tissue marking system of claim 23 wherein said indicator is radioopaque.

26. A tissue marking system configured to mark a tissue sample, the tissue marking system comprising:

an actuator portion movable between an actuated position and anon-actuated position;

at least one indicator including a ball thereon, said ball configured to couple to and rotate within said actuator portion; and a jaw portion coupled to the actuator portion and movable between an open position and a closed position in response to movement of the actuator portion from the actuated position to the non-actuated position, wherein the jaw portion and the actuator portion are transparent to radiographic examination, and wherein the indicator is opaque to radiographic examination.

* * * * *